(12) United States Patent
House

(10) Patent No.: US 7,601,158 B2
(45) Date of Patent: Oct. 13, 2009

(54) DEVICES FOR HANDLING CATHETER ASSEMBLY

(75) Inventor: Jamie Glen House, Colorado Springs, CO (US)

(73) Assignee: Colorado Catheter Company, Inc., Colorado Springs, CO (US)

( * ) Notice: Subject to any disclaimer, the term of this patent is extended or adjusted under 35 U.S.C. 154(b) by 254 days.

(21) Appl. No.: 11/487,487

(22) Filed: Jul. 17, 2006

(65) Prior Publication Data

US 2008/0097463 A1 Apr. 24, 2008

(51) Int. Cl.
*A61F 11/00* (2006.01)
(52) U.S. Cl. ..................................... 606/108
(58) Field of Classification Search ..................................
604/167.01–167.06, 163, 171, 264, 256, 604/523, 533, 534, 535, 537–539; 606/108
See application file for complete search history.

(56) References Cited

U.S. PATENT DOCUMENTS

| | | | |
|---|---|---|---|
| 3,817,251 A * | 6/1974 | Hasson | ........................ 604/26 |
| 4,622,033 A | 11/1986 | Taniguchi | |
| 4,772,275 A | 9/1988 | Erlich | |
| 4,834,710 A | 5/1989 | Fleck | |
| 5,125,893 A * | 6/1992 | Dryden | ........................ 604/500 |
| 5,149,326 A | 9/1992 | Woodgrift et al. | |
| 5,181,913 A | 1/1993 | Erlich | |
| 5,358,495 A | 10/1994 | Lynn | |
| 5,779,670 A | 7/1998 | Bidwell et al. | |
| 5,792,114 A | 8/1998 | Fiore | |
| 5,830,184 A * | 11/1998 | Basta | ........................ 604/104 |
| 5,895,374 A | 4/1999 | Rodsten | |
| 6,053,905 A | 4/2000 | Daignault et al. | |
| 6,059,107 A | 5/2000 | Nosted et al. | |
| 6,090,075 A | 7/2000 | House | |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,537,254 B1 * | 3/2003 | Schock et al. | ................ 604/171 |
| 6,578,709 B1 | 6/2003 | Kavanagh et al. | |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,736,805 B2 | 5/2004 | Israelsson et al. | |
| 6,808,492 B2 * | 10/2004 | Snyder | ....................... 600/114 |
| 6,848,574 B1 | 2/2005 | Israelsson et al. | |
| 6,893,422 B2 | 5/2005 | Altman | |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2003/0018302 A1 | 1/2003 | Kavanagh et al. | |
| 2004/0074794 A1 | 4/2004 | Conway et al. | |
| 2004/0153051 A1 | 8/2004 | Israelsson et al. | |
| 2004/0256264 A1 | 12/2004 | Israelsson et al. | |
| 2005/0015076 A1 | 1/2005 | Giebmeyer et al. | |
| 2005/0109648 A1 | 5/2005 | Kerzman et al. | |
| 2005/0137582 A1 | 6/2005 | Kull-Osterlin et al. | |
| 2006/0025753 A1 | 2/2006 | Kubalak et al. | |

* cited by examiner

*Primary Examiner*—Manuel A Mendez
(74) *Attorney, Agent, or Firm*—Moazzam & Associates, LLC

(57) ABSTRACT

A gripping device for a catheter assembly is disclosed providing enhanced gripping power for the operator of the catheter assembly. The gripping device is situated at the proximal portion of the catheter assembly and the proximal terminus of an external catheter sheath is attached near or to the body of the gripping device.

19 Claims, 3 Drawing Sheets

DEVICES FOR HANDLING CATHETER ASSEMBLY

BACKGROUND OF THE INVENTION

1. Field of the Invention

The present invention relates generally to catheter assemblies. More particularly, the present invention relates to a grip for a proximal portion of a catheter assembly.

2. Background of the Invention

In hospital settings today, nurses often perform urinary catheterization procedures using convenience packs, or pre-assembled kits, which typically contain a vinyl or red latex rubber catheter, a waterproof absorbent underpad, a fenestrated drape, disposable gloves, a sealed packet containing about 22.5 mL of Povidone-Iodine solution, five prepping cotton balls in a disposable tray compartment, a sealed packet containing sterile lubricating jelly, a plastic forceps, a sterile specimen bottle, and a 1000 mL graduated basin. All of these items are packaged together and sterilized.

To perform the catheterization procedure, a nurse opens the tray, dons sterile gloves and places the drape around the patient's genitalia. The Povidone-Iodine packet is opened and poured over the five cotton balls. The packet of lubricating jelly is then opened and squeezed onto a sterile field. The patient's urethral opening is cleansed with the five saturated cotton balls, holding each cotton ball with the forceps. Then, the nurse runs the tip end of the catheter, comprising the first inch or two (about 2.5 cm to about 5 cm) of the insertable portion, through the lubricating jelly. The catheter is then inserted into the patient's urethra and advanced until urine begins to flow through the catheter. The urine is drained into the receptacle and a urine specimen is caught in the specimen bottle if needed. The catheter is then removed and all the aforementioned items are discarded. Care must be taken during these steps to maintain sterile technique in order to reduce the risk of urinary tract infection. Because multiple steps are involved in the catheterization procedure and meticulous attention to maintain sterile technique is required, a nurse typically spends a significant amount of time (e.g., 10-15 minutes) carrying out each catheterization. This basic procedure is used in virtually every inpatient hospital around the world, and has remained essentially the same for 50 years.

Thus, there is a need in the healthcare industry for a simplified and streamlined inpatient catheterization procedure to eliminate the steps that compromise sterile technique and reduce the amount of time spent per patient on the catheterization process.

SUMMARY OF THE INVENTION

The current techniques for inpatient catheterization are inefficient. In conventional catheterization techniques, a small portion (about 1"-2") of a catheter tip is manually lubricated before insertion into a patient's urethra. While holding the patient's genitalia with one hand, the nurse grasps the catheter body with the other hand and guides the lubricated catheter tip into the patient's urethra. Such contact with the catheter may result in contamination if proper sterile technique is not used. Additionally, the nurse has only a limited ability to guide the catheter into the patient's urethra and insert the catheter farther into the patient's urethra since only one hand is free to perform these operations. Thus, the inefficiency in conventional urinary catheterization results from the many meticulous steps required to maintain sterile technique along with the operator's inability to effectively guide and insert the catheter. In order to address this healthcare problem, the present invention provides techniques for more easily gripping and manipulating a catheter assembly while maintaining a sterile procedure even though sterile technique is not employed. More specifically, the present invention proposes a gripping device on a proximal portion of a catheter assembly to increase dexterity of the catheter assembly with an introducer tip being inserted into the patient's urethra prior to catheter insertion thereby freeing the operator's other hand to guide and insert the catheter into the patient's urethra.

In one exemplary embodiment, the present invention is a gripping device for a catheter assembly. The device includes a gripping body situated at a proximal portion of a catheter assembly; the gripping body including an adhesive portion for sheath attachment, and an apertured center portion for catheter guidance.

In another exemplary embodiment, the present invention is a gripping device for a catheter assembly. The device includes a cylindrically shaped gripping body with concave lateral portions with a distal half of the gripping body located within a sheath and a proximal half of the gripping body situated external to the sheath; a collar located on a middle portion of the gripping body, the collar receiving a proximal terminus of the sheath; a throughbore positioned in a middle portion of the gripping body so as to allow guidance of a catheter therethrough; and an apertured center portion of the gripping body comprising a slitted penetrable barrier including multiple flaps, the barrier piercable by the catheter upon insertion.

In yet another exemplary embodiment, the present invention is a catheter assembly. The assembly includes a gripping body grippable by an operator's hand; a connected introducer body proximal to the gripping body; and a catheter situated within a surrounding sheath which is grippable by the operator's other hand.

In one of the exemplary embodiments of the present invention, a proximal end of the catheter assembly is equipped with an introducer, and a guiding portion composed of a cylindrical gripping device attached to an external protective sheath. With this exemplary embodiment, the operator is provided with a gripping surface which may be textured (e.g, corrugated in a particular pattern) which can be used to stabilize the catheter assembly during insertion of the catheter through the introducer into the patient's urethra.

In another exemplary embodiment, the gripping device is conical in shape with a textured or corrugated surface in order to provide an alternative design to enhance the operator's dexterity.

In yet another exemplary embodiment, the gripping device is a part of an external textured collar where the sheath is attached. This exemplary embodiment may include an internal collar as well.

In yet another embodiment of the present invention, the gripping device is cylindrically shaped with concave lateral portions so as to increase operator dexterity. This exemplary embodiment may be composed of two introducer portions as well for optimal catheter guidance.

As used herein and throughout this disclosure, and in order to understand the directional aspects of this invention, "proximal" refers to the section of the device that is closer to the patient's body (e.g., urethra) while "distal" refers to the section of the device that is farther away from the body, or closer to the back-end of the catheter assembly used to connect to a collection receptacle.

DETAILED DESCRIPTION OF THE INVENTION

The present invention provides for catheter and catheter assemblies with easy-gripping handle portions such that such catheter and catheter assemblies are more readily manipulated in and around the body. In particular embodiments and examples presented herein, such catheters are described with respect to urinary catheterization but it must be noted that such handles and grips according to the present invention are not limited to urinary catheters alone but may be applicable to any catheter and catheter assembly that could benefit from the use of such handles or grips. Furthermore, the present invention allows for more efficient and secure handling of catheter and catheter assemblies to decrease the time required for and increase the safety and reliability of catheterization and associated procedures.

Figure 1:
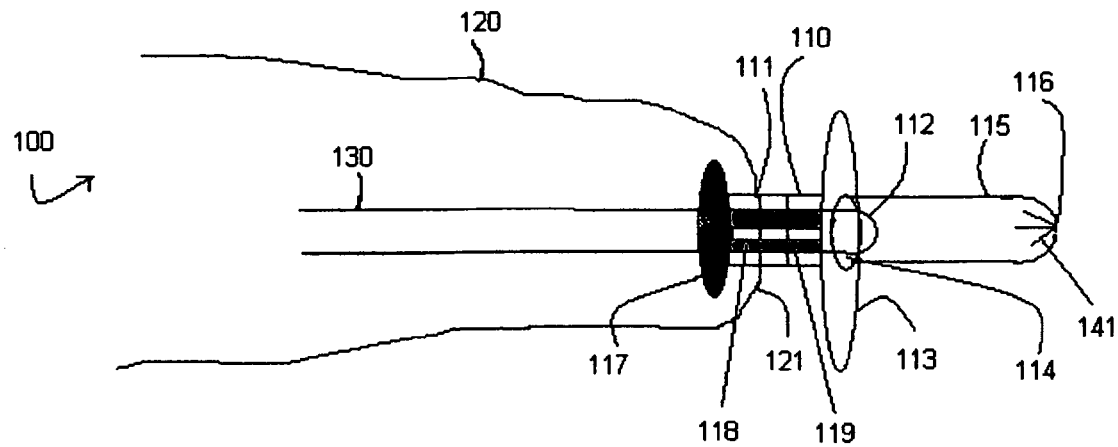
FIG. 1 shows a side view of a cylindrically shaped gripping device according to an exemplary embodiment of the present invention.

An exemplary embodiment of the present invention as used in catheter assembly 100 is shown in FIG. 1. Assembly 100 includes a cylindrically shaped gripping body 110, a protective sheath 120, a catheter 130, an optional first collar 117, a second collar 113, and an introducer 115. The gripping body 100 may also contain one or more venting channels 119 to assist in the movement of the sheath. The venting channels 119 can further enclose optional filters or membranes 118. The catheter 130 may be composed of a conventional material commonly used in the catheter arts or it may be composed of a hydrophilic material in order to further lubricate the catheter 130.

The protective sheath 120 may be attached to the gripping body 110 at attachment site 111 at a proximal terminus 121 of the protective sheath 120 as depicted in FIG. 1. In this exemplary embodiment, about half of the gripping body 110 is situated inside the protective sheath 120 while the other half of the gripping body 110 is situated outside the protective sheath 120. The optional venting channels 119 may be longitudinal cut-outs running the length of the gripping body 110 such that the protective sheath 120 makes contact with the surface of the cut-outs thereby forming a space between the attachment site 111 and the bottom of the longitudinal cut-outs such that gas (e.g., built-up air) is able to escape from inside the protective sheath 120 to the external environment during manipulation of catheter assembly 100. The optional venting channels 119 may be covered by optional filters or membranes 118 so that care is taken to maintain a contamination free environment. The optional filters or membranes 118 may be composed of a standard material commonly used in the catheter arts such that they are permeable to gases (e.g., $N_2$ and $O_2$) thereby allowing air to escape through the optional filters or membranes 118 from the inside of the protective sheath 120 to the external environment. Such a permeable material may include, but is not limited to, polyimide copolymers and may effectively keep out bacterial or viral contaminants from inside the catheter assembly 100.

The protective sheath 120 may also be attached via attachment site 111 on any other portion of the gripping body 110 including the region spanning from and including the distal, backside of optional first collar 117 to the proximal, front side of the second collar 113. Thus, the gripping body 110 may be entirely situated external or internal to the protective sheath 120. These variations would not utilize the optional venting channels 119. The protective sheath 120 can be attached at attachment site 111 to the gripping body 110 by various attachment methods known to one having ordinary skill in the art as long as care is taken to maintain a contamination free environment (e.g., adhesion, heat sealing, snap collaring). The protective sheath 120 may serve to maintain catheter sterility and provide a chamber for additional lubricant or aqueous solution for the catheter 130.

In the assembled, unused or pre-used form of catheter assembly 100, the catheter tip 112 may be retained proximal to a distal end of the gripping body 110 (which could be at optional first collar 117), and distal to the proximal tip 116 of the introducer 115. Thus, the catheter tip 112 may be situated anywhere inside the gripping body 110 distal to aperture 114 or anywhere inside the introducer 115 proximal to aperture 114. Such a position for the catheter tip 112 allows for the catheter 130 from falling back out of the body 110 and into the sheath 120. Also, there could be slits or a membrane at the far distal end of the body 110 or at any location along the body including the aperture at 112. This again would further act to keep the catheter 130 from falling backwards into the sheath 120.

In order to guide the catheter 130, the optional first collar 117 may contain a throughbore of a slightly larger diameter than catheter 130, and it may also contain a slitted diaphragm or membrane (not shown) apertured in such a way so as to provide the catheter 130 a stable and controlled passageway (e.g., a slitted design with 4 flaps). This slitted diaphragm or membrane (not shown) at the distal, backside of optional first collar 117 may be pierced by the catheter tip 112 in the unused form and may function to prevent the catheter 130 from falling back into the protective sheath 120. Also, the catheter assembly 100 may have other slitted diaphragms or membranes (not shown) along the inside of the gripping body 110, at the aperture 114, and along inside the inside of introducer 115. These slitted diaphragms or membranes (not shown) may further act to prevent the catheter 130 from falling back into the protective sheath 120 and out of the gripping body 110, and may also help stabilize and secure the passage of catheter 130 through catheter assembly 100. The optional first collar 117 may provide enhanced operator dexterity of the catheter assembly 100 and can be used to support the bottom of the operator's hand during catheter insertion. The gripping body 110 may be of a length such that the operator is able to grasp the gripping body 110 with at least the index finger and thumb. The gripping body 110 may also be textured or corrugated to provide increased operator dexterity as well.

During a routine catheterization process, the gripping body 110 may be grasped such that the operator's hand and fingers are distal to and underneath the second collar 113 or such that the operator's index finger and thumb are on the surface of second collar 113 or on the patient's penis while taking care to minimize contamination of the catheter 130. The operator's other hand may be used to grasp the patient's genitalia as well. The introducer 115 may be introduced into the patient's urethra to stabilize the catheter assembly 100 such that the operator is able to release the patient's genitalia and use the newly freed hand to guide and insert the catheter 130 through the gripping body 110, into the introducer 115, and then into the patient's urethra. The inside of the gripping body 110 may have a slightly larger diameter than the diameter of the catheter 130 to allow for catheter 130 to pass through smoothly and unimpeded. Additionally, the inside of the gripping body 110 may contain a lubricant chamber to keep lubricated the portion of catheter 130 just distal to the catheter tip 112. This chamber can be formed by a variety of ways, including, for example, that shown by U.S. Pat. No. 6,090,075, entitled "Disposable Urinary Catheterization Assembly," issued on Jul. 18, 2000, and hereby incorporated by reference herein in its entirety. Such chamber may include a compartmentalized portion housing the lubricant or aqueous solution with a penetrable distal diaphragm or membrane for the catheter tip 112 to pierce and thereby be exposed to the lubricant or aqueous solution.

The catheter 130 is then guided through an aperture 114 of the second collar 113, which may be textured or corrugated to provide increased operator dexterity. The gripping body 110 may either be connected to the second collar 113 and introducer 115 (e.g, forming a single proximal piece) or the gripping body 110 may be separate from the second collar 113 and the introducer 115 with the second collar 113 and the introducer 115 being attachable to the gripping body 110 (e.g., forming two or more distinct proximal pieces). The aperture 114 of second collar 113 may be slitted (e.g., forming four flaps) or contain a slitted diaphragm or membrane (not shown) to allow a more stable and controlled passage for the proximal tip 112 and the rest of the body of the catheter 130. The slitted diaphragm or membrane (not shown) would prevent lubricant or aqueous solution from prematurely entering into the introducer 115 thereby providing a lubricant chamber inside gripping body 110.

Next, the catheter tip 112 may be guided through the introducer 115, which has a slightly larger diameter than the catheter 130 and may contain lubricant or aqueous solution as well to allow the catheter 130 to pass smoothly therethrough. The introducer 115 may also contain a single or multiple slitted diaphragms or membranes (not shown) which can enhance dexterity and catheter guidance. The proximal tip 116 of introducer 115 may have a slitted tip portion 141 (e.g., forming four or more flaps) to provide a controlled passageway for the catheter tip 112 and catheter 130. If lubricant or aqueous solution is stored in the introducer 115, then a removable seal at the slitted tip portion 141 would contain the lubricant or aqueous solution inside the introducer 115 providing a contamination-free housing portion.

Use and introduction of the catheter 130 of catheter assembly 100 into a patient, for example, within the urethral opening, is facilitated by the inclusion of the gripping body 110 located substantially between, or "book-ended" by, the optional first collar 117 and the second collar 113. Such gripping body 110 being securely fastened to the catheter assembly 100 allows the user, be it caretaker or patient, to more securely hold the assembly in proper place and more accurately direct the catheter tip 112 into the patient's urethra.

Figure 2:
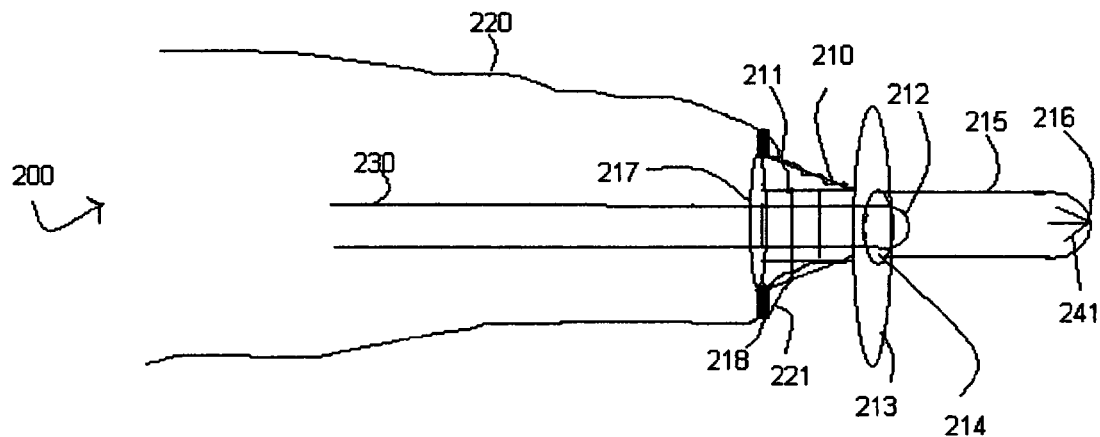
FIG. 2 shows a side view of a conically shaped gripping device according to an exemplary embodiment of the present invention.

Another exemplary embodiment of the present invention incorporated into a catheter assembly 200 is shown in FIG. 2, and includes a conically shaped gripping body 210 with optional projections 218, a catheter 230, a collar 213, an introducer 215, and a protective sheath 220. The catheter 230 may be composed of a conventional material regularly used in the art or it may be composed of a hydrophilic material in order to further lubricate the catheter 230. Also, the gripping body 210 may be textured or corrugated to enhance operator dexterity. The protective sheath 220 functions to maintain catheter sterility and provide a volume for additional catheter lubricant or aqueous solution.

The protective sheath 220 may be attached to the gripping body 210 at attachment site 211 at the proximal terminus 221 of the protective sheath as depicted in FIG. 2. The protective sheath 220 may also be attached via attachment site 211 to any other portion of the gripping body 210 ranging from and including the distal surface 217 to the proximal, front side of collar 213. Thus, the gripping body 210 may be entirely situated external or internal to the protective sheath 220 as well. The connection at attachment site 211 may be made possible by various attachment methods known to one having ordinary skill in the art as long as care is taken to maintain a contamination free environment.

The gripping body 210 may also possess optional projections 218 to provide a better surface for attachment site 211 or to provide increased operator dexterity of the gripping body 210. These optional projections 218 may be individual and independent tabs located at numerous positions along the circular distal end of the gripping body 210. Alternatively, the optional projections 218 may be a single ring spanning and covering the entire distal end of gripping body 210 and acting as a small collar positioned substantially perpendicularly to the axis of the catheter 230. In either way described or other ways possible, the optional projections 218 could improve dexterity of the operator's hand and additionally provide a better seal between the proximal terminus 221 of the protective sheath 220 and the gripping body 210. The distal surface 217 of the gripping body 210 may contain a throughbore with a slightly larger diameter than catheter 230. The distal surface 217 may also contain a slitted diaphragm or membrane (not shown) which may act to prevent the catheter 230 from falling back into the protective sheath 220, and also act to provide the catheter 230 with a stable and secure passageway through the gripping body 210. The gripping body 210 may be of a length such that the operator is able to grasp the gripping body 210 with at least the index finger and thumb. The gripping body 210 may also be textured or corrugated to provide increased operator dexterity as well.

During catheter insertion, the catheter 230 is introduced through the distal surface 217 of the gripping body 210. The gripping body 210 may be grasped such that the operator's hand and fingers are distal to and underneath the collar 213 or such that the operators index finger and thumb are on the surface of collar 213 or on the patient's penis while taking care to minimize contamination of the catheter 230. The operator's other hand may be used to grasp the patient's genitalia as well. The introducer 215 may be introduced into the patient's urethra to stabilize the catheter assembly 200 such that the operator is able to release the patient's genitalia and use the newly freed hand to guide and insert the catheter 230 through the gripping body 210, into the introducer 215, and then into the patient's urethra. In order to facilitate the passage of catheter 230 through the gripping body 210, the gripping body 210 may contain a lubricant or aqueous solution, or it may house a lubricant chamber. Such chamber may include a compartmentalized portion housing the lubricant or aqueous solution with a penetrable distal diaphragm or membrane for the catheter tip 212 to pierce and thereby be exposed to the lubricant or aqueous solution. The patent cited above, and incorporated by reference herein, may be consulted to consider types of lubricant chambers that may be used.

The gripping body 210 may be connected to the collar 213 and the introducer 215 (e.g., forming a single proximal piece) or the gripping body 210 may be separate from the collar 213 and introducer 215 with the collar 213 and the introducer 215 being attachable to the gripping body 210 (e.g., forming two or more separate proximal pieces). The catheter tip 212 is then manipulated through the aperture 214 of collar 213 during catheter insertion. The collar 213 may be textured or corrugated so as to provide additional operator dexterity for the operator's index finger and thumb. The aperture 214 may be a throughbore of a slightly larger diameter than the catheter 230. The aperture 214 may also contain a slitted diaphragm or membrane (not shown) to provide a more stable and controlled passageway for the catheter 230. The catheter 230 is then guided through the introducer 215, which has a slightly larger diameter than catheter 230 and may contain lubricant or aqueous solution as well. The introducer may also contain a single or multiple slitted diaphragms or membranes (not shown) to enhance dexterity and catheter guidance.

The proximal tip 216 of introducer 215 may have a slitted tip portion 241 (e.g., forming four or more flaps) to provide a controlled passageway for the catheter tip 212 and catheter 230. If lubricant or aqueous solution is stored in the introducer 215, then a removable seal at the slitted tip portion 241 would contain the lubricant or aqueous solution inside the introducer 215 providing a contamination-free housing portion.

In the pre-used form of catheter assembly 200, the catheter tip 212 may be retained proximal to distal surface 217 and distal to the proximal tip 216 of the introducer 215 similar to as described above.

The particular conical gripping body 210 presented in the assembly 200 shown in FIG. 2 has many advantages. For example, the conical shape allows a better grip of the assembly 200 by taking into account the tapered design of the conical shape and its accommodation of the hand. The conical shape of the grip 210 allows the user's hand to lean proximally or exert additional pressure or gripping power to the proximal end of the grip 210 because the hand and fingers naturally slide from a wider cross section of the grip 210 to a narrower cross section. Thus, the user's hand is naturally forced to exert better gripping power at the narrower, and more proximal end, of the grip 210, thereby allowing additional accuracy during the insertion process of the catheter tip 212 into the urethra. However, the present invention is not limited to a conical shape that is presented in FIG. 2, and may also include a conically shaped gripping body 210 with its tapered end being reversed with a larger diameter end positioned more proximal and a narrower diameter end positioned more distal.

Figure 3:
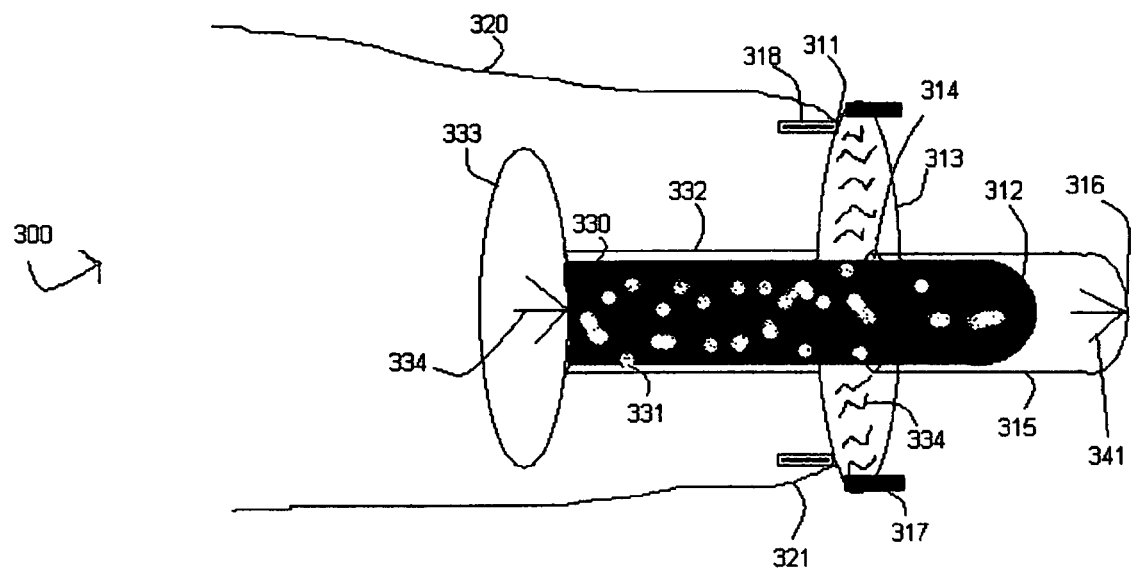
FIG. 3 shows a side view of a textured collar proximal gripping device according to an exemplary embodiment of the present invention.

Another exemplary embodiment of the present invention incorporated into a catheter assembly 300 is shown in FIG. 3. The assembly 300 includes a catheter 330, an optional first collar 333, a guide portion 332, a second collar 313 with a textured surface 334 for enhancing gripping power, proximal projections 317, distal projections 318, a sheath 320, and an introducer 315. The distal projections 318 and proximal projections 317 may be depicted as shown in FIG. 3 as isolated, axial projections or they may be circumferential such that they form single rings spanning and covering either surface of the second collar 313 and acting as small collars positioned substantially perpendicularly to the axis of the catheter 330.

The catheter 330 may be constructed of a conventional material used in the art or it may be composed of a hydrophilic material in order to further lubricate the catheter 330. The protective sheath 320 may be attached to the second collar 313 at attachment site 311 at the proximal terminus 321 of the protective sheath 320 as depicted in FIG. 3. The protective sheath 320 functions to maintain a sterile environment for the catheter 330 and also to house a volume of lubricant or aqueous solution for the catheter 330. The attachment site 311 may be sealed to the second collar 313 by various adhesive methods known to one having ordinary skill in the art as described above as long as care is taken to maintain a contamination free environment. Alternatively, the protective sheath 320 may be attached via attachment site 311 anywhere between and including the distal side of optional first collar 333 to the proximal side of second collar 313. In this way, the optional first collar 333 along with the guide portion 332 and second collar 313 can be situated outside of the protective sheath 320, or the optional first collar 333 along with a segment of the guide portion 332 can be situated inside the protective sheath 320 as well.

The catheter assembly 300 may include a guide portion 332 attached to a distal side of the second collar 313. The guide portion 332 may be of a slightly larger diameter than the catheter 330. An optional first collar 333 may be attached to the guide portion 332 to provide increased operator dexterity of the catheter 330 and catheter assembly 300. The optional first collar 333 may contain a throughbore of a slightly larger diameter than catheter 330 and it may contain a diaphragm or membrane with a slitted portion 334 forming multiple flaps to enhance catheter manipulation during insertion and also to prevent the catheter from falling back into the protective sheath 320. The guide portion 332 may also contain a single or multiple slitted diaphragms or membranes (not shown) inside of its length which serve to enhance catheter stabilization and guidance. There may be stored lubricant 331 or aqueous solution, or a lubricant chamber within the guide portion 332 as well. The lubricant 331 is depicted in FIG. 3 as morphous gel-like particles for the sake of simplicity. The lubricant 331 can be in this well-defined form as depicted or it can be more aqueously defined. The lubricant chamber can vary in design but may include a compartmentalized portion housing the lubricant or aqueous solution with a penetrable distal diaphragm or membrane for the catheter tip 312 to pierce and thereby be exposed to the lubricant or aqueous solution.

During catheterization, the optional first collar 333 and the guide portion 332 may be grasped such that the operators hand and fingers are distal to and underneath the second collar 313 or such that the operator's index finger and thumb are on the surface of second collar 313 or on the patient's penis while taking care to minimize contamination of the catheter 330. The operator's other hand may be used to grasp the patient's genitalia as well. The optional first collar 333 may serve as a backstop to the operator's hand or it may simply increase the operator's dexterity and handling of the catheter assembly 300. The introducer 315 may be introduced into the patients urethra to stabilize the catheter assembly 300 such that the operator is able to release the patient's genitalia and use the newly freed hand to guide and insert the catheter 330 through the guide portion 332 into the introducer 315, and then into the patient's urethra. The aperture 314 may be of a slightly larger diameter than catheter 330 and it may contain a slitted diaphragm or membrane (not shown) forming multiple flaps for the catheter to pass smoothly therethrough. The second collar 313 may possess proximal projections 317 to prevent the operator's index finger and thumb from slipping off. The second collar 313 may also possess distal projections 318 to provide a better surface for attachment site 311 or to provide increased operator dexterity.

The catheter tip 312 is then manipulated through aperture 314 into the introducer 315. The introducer 315 may contain a single or multiple slitted diaphragms or membranes (not shown) which serve to enhance catheter stabilization and guidance. The introducer 315 may also contain lubricant 331 or aqueous solution. The introducer 315 may be of a slightly larger diameter than catheter 330 and may possess a slitted tip portion 341 forming multiple flaps. If lubricant or aqueous solution is stored within the introducer 315, then a seal may placed on the proximal tip 316 to keep the catheter 330 sterile and provide a barrier preventing contamination.

In the pre-used form of catheter assembly 300, the catheter tip 312 may be retained proximal to the optional first collar 333 and distal to the proximal tip 316 of the introducer 315 similar to as described above.

Use and introduction of the catheter 330 of catheter assembly 300 into a patient, for example, within the urethral opening, is facilitated by the inclusion of the second collar 313 located substantially outside of the protective sheath 320. The user may also hold the guide portion 332 or optional first collar 333 through force exerted on the surface of the protective sheath 320. Because the guide portion 332 may securely fasten the optional first collar 333 to the second collar 313, a "dumbbell" shape is created to serve as a substantially rigid holding point for a user to hold onto while directing the catheter 330 into a body cavity, such as the urethral opening. The guide portion 332 may be of a length such that the operators can grasp it using the thumb and index finger.

Figure 4:
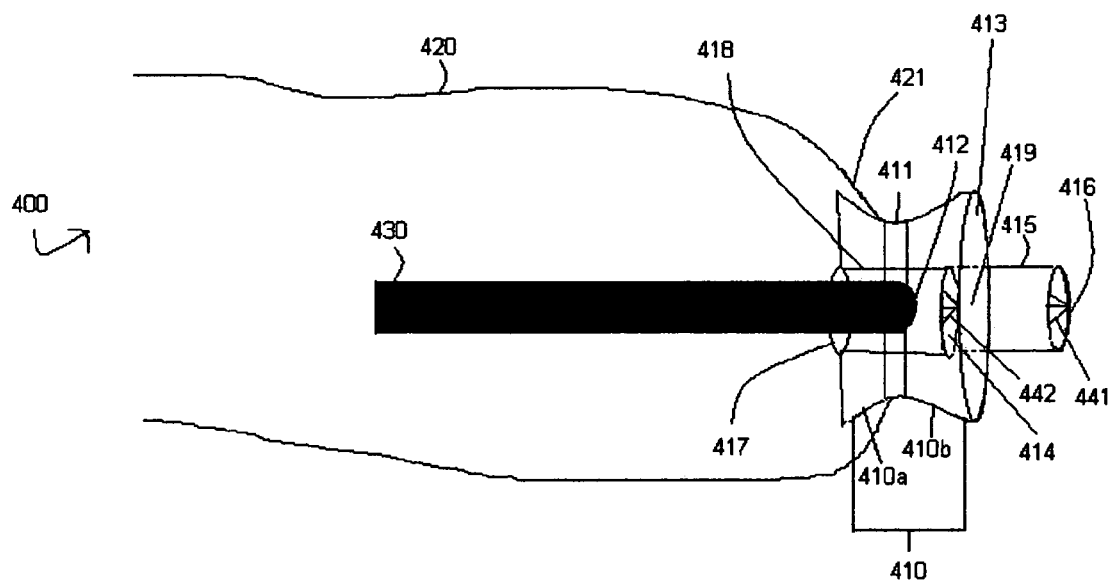
FIG. 4 shows a side view of a cylindrically shaped gripping device with lateral concave portions according to an exemplary embodiment of the present invention.

Another exemplary embodiment of the present invention incorporated into a catheter assembly 400 is shown in FIG. 4. The assembly 400 includes a cylindrically shaped gripping body 410 with concave lateral portions, a seal 411, a catheter 430, a first introducer 418, a second introducer 415, and a protective sheath 420. The catheter 430 may be constructed from a conventional material regularly used in the art or it may be composed of a hydrophilic material in order to further lubricate the catheter 430.

The seal 411 divides the gripping body 410 into a first gripping portion 410a and a second gripping portion 410b as depicted in FIG. 4. However, the seal may be positioned anywhere along the gripping body 410 from and including the distal side of the first gripping portion 410a to the surface of collar 413. The seal 411 may be accomplished by various attachment methods as described above while taking care to maintain a contamination free environment. The seal 411 may adhere the proximal terminus 421 of the protective sheath 420 to the gripping body 410, thus preserving a sterile internal environment within the protective sheath 420. The protective sheath 420 also functions to hold a volume of lubricant or aqueous solution for catheter 430. The first gripping portion 410a may be located within the protective sheath 420 while the second gripping portion 410b may located outside of the protective sheath 420 as depicted in FIG. 4. Alternatively, the first gripping portion 410a and the second gripping portion 410b may be located entirely inside of or outside of the protective sheath 420 depending on the location of seal 411.

In the pre-used form of catheter assembly 400, the catheter tip may be retained proximal to the first aperture 417 and distal to the proximal tip 416. The first aperture 417 may be of a slightly larger diameter than the catheter 430 and it may contain a slitted diaphragm or membrane (not shown) forming multiple flaps thereby preventing the catheter 430 from falling back into the protective sheath 420 and also enhancing catheter stability. The first introducer 418 may have a throughbore of a slightly larger diameter than the catheter 430 to provide a smooth passageway for catheter 430. The first introducer 418 could be either connected to the collar 413 and gripping body 410, or the first introducer 418 could be a separate piece distinct from the gripping body 410 with its own attachment site to the first gripping portion 410a. The gripping body 410 could also be a detachable piece with the second gripping portion 410b being attached just proximal to the seal 411. In this way, the second gripping portion 410b could be detached from the gripping body 410 so that additional lubricant or aqueous solution could be added to the catheter 430 or inside the second introducer 415 if necessary while maintaining a sterile internal environment.

During use, the operator guides the catheter 430 through the first introducer 418 from just proximal to the first aperture 417 to the second aperture 414 of the collar 413. The first introducer 418 may also contain inside its length a single or multiple slitted diaphragms or membranes (not shown) to enhance catheter stability. The first gripping portion 410a and the second gripping portion 410b may be of a length such that the operator's hand and fingers may grasp distal to and underneath the collar 413. The operator may also grasp the surface of collar 413 with the index finger and thumb or the operator may grasp the patient's penis with the index finger and thumb while taking care to minimize contamination of the catheter 430. The operator's other hand may be used to grasp the patient's genitalia as well. The first gripping portion 410a and the second gripping portion 410b may both serve as backstops to the operator's hand or they may simply increase the operator's dexterity and handling of the catheter assembly 400. The second introducer 415 may be introduced into the patient's urethra to stabilize the catheter assembly 400 such that the operator is able to release the patient's genitalia and use the newly freed hand to guide and insert the catheter 430 through the first introducer 418 into the second introducer 415, and then into the patient's urethra. The second aperture 414 may be of a slightly larger diameter than the catheter 430 and it may contain a slitted diaphragm or membrane 442 forming multiple flaps on the center portion 419 of the collar 413. The first introducer 418 may contain lubricant or aqueous solution, or a lubricant chamber with the slitted diaphragm or membrane 442 in the second aperture 414 on collar 413 acting to prevent lubricant leakage. Such chamber may include a compartmentalized portion housing the lubricant or aqueous solution with a penetrable distal diaphragm or membrane for the catheter tip 412 to pierce and thereby be exposed to the lubricant or aqueous solution.

The catheter 430 is then guided through the second aperture 414 and into the second introducer 415. The second introducer 415 may be situated on top of collar 413 which may also be textured or corrugated to enhance gripping power. The second introducer 415 may also contain lubricant or aqueous solution or a lubricant chamber. The second introducer 415 may also contain a single or multiple slitted diaphragms or membranes (not shown) along the inside of its length to enhance catheter stability and guidance. The proximal tip 416 of the second introducer 415 may contain a slitted tip portion 441 forming multiple flaps for catheter guidance. To keep the lubricant and catheter 430 sterile, a removable seal could be placed on the proximal tip 416. A variation of the exemplary embodiment of catheter assembly 400 shown in FIG. 4 would lack the first introducer 418.

Figure 5:
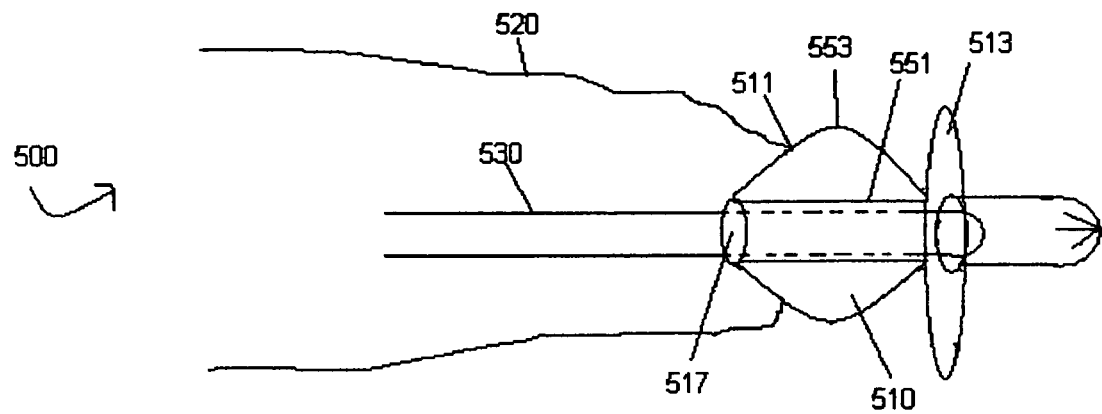
FIG. 5 shows a side view of a smooth transition bipyramidal shaped gripping device according to an exemplary embodiment of the present invention.

Another exemplary embodiment of the present invention incorporated into a catheter assembly 500 is shown in FIG. 5. For the sake of simplicity, only the gripping body 510 along with the components particularly relevant to this embodiment are labeled. The corresponding components from FIGS. 1-4 not labeled in FIG. 5 and the parameters associated with such components are hereby incorporated into FIG. 5. In this exemplary embodiment, the gripping body 510 may be bipyramidal in shape with the rounded apices 553 of the pyramidal shapes forming convex lateral portions of the gripping body 510. The gripping body 510 may be textured or corrugated to provide an enhanced gripping surface. The gripping body 510 may also contain a throughbore 551 of a diameter slightly larger than the diameter of catheter 530 such that catheter 530 is able to pass through the throughbore 551 in a controlled and smooth fashion. The throughbore 551 may contain a single or multiple slitted diaphragms or membranes (not shown) along the inside of its length in order to enhance catheter guidance. The distal end of the gripping body 510 may also contain an aperture 517 which may contain a slitted diaphragm or barrier (not shown) in order to prevent the catheter 530 from falling back into the protective sheath 520 and in order to enhance catheter guidance. The attachment site 511 may be located distal to rounded apices 553 as depicted in FIG. 5 or the attachment site 511 may be located anywhere from and including the most distal portion of the gripping body 510 (e.g. surrounding aperture 517) to the surface of collar 513. Other combinations, shapes and sizes of the gripping body 510 are also possible and within the scope of the present disclosure.

Figure 6:
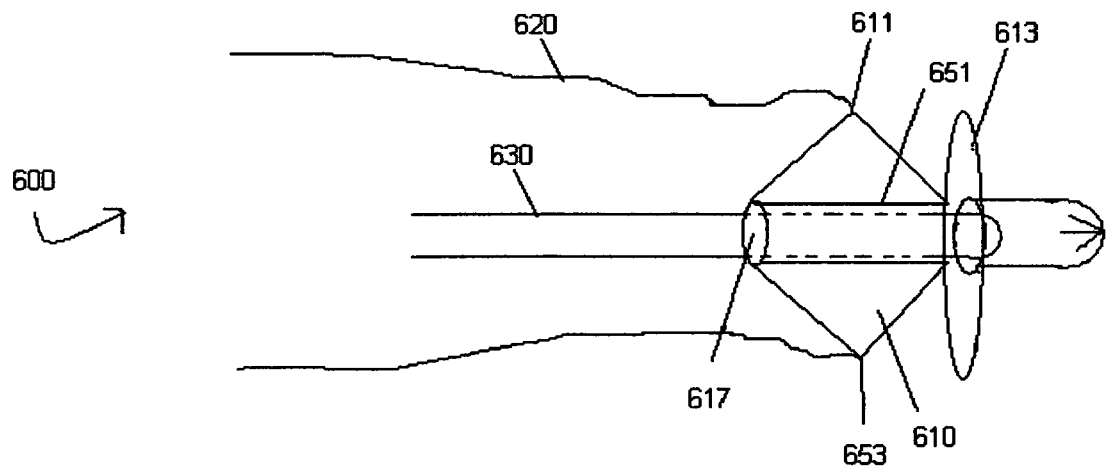
FIG. 6 shows a side view of a sharp transition bipyramidal shaped gripping device according to an exemplary embodiment of the present invention.

Yet another exemplary embodiment of the present invention incorporated into a catheter assembly 600 is shown in FIG. 6. For the sake of simplicity, only the gripping body 610 along with the components particularly relevant to this embodiment are labeled. The corresponding components from FIGS. 1-4 not labeled in FIG. 6 and the parameters associated with such components are hereby incorporated into FIG. 6. In this exemplary embodiment, the gripping body 610 may be bipyramidal in shape with the sharp apices 653 of the pyramidal shapes forming convex lateral portions of the gripping body 610. The gripping body 610 may be textured or corrugated to provide an enhanced gripping surface. The sharp apices 653 may be formed from a 90 degree angle as shown in FIG. 6. The gripping body 610 may also contain a throughbore 651 of a diameter slightly larger than the diameter of catheter 630 such that catheter 630 is able to pass through the throughbore 651 in a controlled and smooth fashion. The throughbore 651 may contain a single or multiple slitted diaphragms or membranes (not shown) along the inside of its length in order to enhance catheter guidance. The distal end of the gripping 610 may also contain an aperture 617 which may contain a slitted diaphragm or barrier (not shown) in order to prevent the catheter 630 from falling back into the protective sheath 620 and in order to enhance catheter guidance. The attachment site 611 may be located distal to sharp apices 653 as depicted in FIG. 5 or the attachment site 611 may be located anywhere from and including the most distal portion of the gripping body 610 (e.g. surrounding aperture 617) to the surface of collar 613. Other combinations, shapes and sizes of the gripping body 610 are also possible and within the scope of the present disclosure.

All of the materials used for the present invention may be comprised of artificial or naturally occurring non-degradable biocompatible polymer compounds such that the materials used for the present invention serve the functions delineated in this application. Such compounds can include, but are not limited to, polyester based biocompatible polymers, nylon-based biocompatible polymers, latex based biocompatible polymers, Teflon, polytetrafluoroethylene (PTFE) polymers, polyvinyl chloride (PVC) polymers, silicone polymers, polyurethane polymers, silicone polyurethane polymers, ethylene-vinyl acetate copolymers, polyethylene polymers, and thermoplastic polymers. The catheters themselves may also be composed of a hydrophilic compound formed from the reaction of an epoxy containing polyvinyl pyrrolidone with a polyamino compound. The lubricating material includes but is not limited to an aqueous solution or a hydrogel formed as the reaction product of a siloxane containing macromer, one hydrophilic polymer, and one compatibilizing component. The lubricating material also may be composed of a biocompatible antibacterial agent such as a 4-quinolone agent to prevent contamination.

The manufacturing methods that can be employed for the present invention include, but are not limited to, conventional techniques used in the industry to produce similar function products, as known by a person having ordinary skill in the art.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A gripping device for a urinary catheter assembly, the device comprising:
   a gripping body situated at a proximal portion of a urinary catheter assembly; the gripping body including an adhesive portion for sheath attachment, and
   a throughbore in the gripping body oriented for catheter guidance;
   wherein the gripping body prevents movement of a user's finger and thumb with respect to the gripping body along a longitudinal axis of the urinary catheter assembly while the gripping body is grasped with the user's finger and thumb.

2. The device of claim 1, wherein the gripping body is cylindrically shaped.

3. The device of claim 1, wherein the gripping body is conically shaped.

4. The device of claim 1, wherein the gripping body is cylindrically shaped with concave lateral portions.

5. The device of claim 1, wherein the gripping body is bipyramidal in shape with convex lateral portions.

6. The device of claim 1, wherein a portion of the gripping body is situated internal to the sheath, and an external portion of the gripping body is used to grip the catheter assembly.

7. The device of claim 1, wherein the gripping body is situated internal to the sheath, and is used to grip the catheter assembly.

8. The device of claim 1, wherein a distal terminus of the gripping body contains an internal collar to promote gripping and adhesion with a proximal terminus of the sheath.

9. The device of claim 8, wherein the internal collar has lateral extensions.

10. The device of claim 1, wherein the adhesive portion is located on a midline of the gripping body where a proximal terminus of the sheath is attached.

11. The device of claim 1, wherein the adhesive portion is located on a distal portion of the gripping body where a proximal terminus of the sheath is attached.

12. The device of claim 1, wherein the adhesive portion is located on a proximal portion of the gripping body where a proximal terminus of the sheath is attached.

13. The device of claim 1, wherein the gripping body is an external collar.

14. The device of claim 13, wherein the external collar is textured or corrugated.

15. The device of claim 1, wherein an apertured center portion of the gripping body includes multiple flaps formed from at least one slit.

16. The device of claim 1, wherein the gripping body has longitudinal channels cut into its body.

17. The device of claim 1, wherein in a pre-used position, a proximal tip of a catheter is retained proximal to a distal end of the gripping body and distal to an opening of an introducer attached thereto.

18. A gripping device for a urinary catheter assembly, the device comprising:
   a cylindrically shaped gripping body with concave lateral portions with a distal portion of the gripping body located within a sheath and a proximal portion of the gripping body situated external to the sheath;
   a collar located on a middle portion of the gripping body, the collar receiving a proximal terminus of the sheath;
   a throughbore positioned in a middle portion of the gripping body so as to allow guidance of a catheter therethrough; and
   an apertured center portion of the gripping body comprising a slitted penetrable barrier including multiple flaps, the barrier piercable by the catheter upon insertion;
   wherein the gripping body prevents movement of a user's finger and thumb with respect to the gripping body along a longitudinal axis of the urinary catheter assembly while the gripping body is grasped with a user's finger and thumb.

19. The device of claim 18, wherein the cylindrically shaped gripping body is textured or corrugated.

* * * * *